United States Patent
Hurtak et al.

(10) Patent No.: US 6,458,088 B1
(45) Date of Patent: *Oct. 1, 2002

(54) GLASS CORE GUIDEWIRE COMPATIBLE WITH MAGNETIC RESONANCE

(75) Inventors: Wenzel Franz Hurtak, Roden; Frans Mous, Drachten; Cornelis Philipus Nap, Zevenhuizen, all of (NL)

(73) Assignee: Cordis Corporation, Miami Lakes, FL (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/381,703
(22) PCT Filed: Mar. 27, 1998
(86) PCT No.: PCT/US98/06080
  § 371 (c)(1),
  (2), (4) Date: Sep. 22, 1999
(87) PCT Pub. No.: WO98/42268
  PCT Pub. Date: Oct. 1, 1998

(30) Foreign Application Priority Data

Mar. 27, 1997 (NL) ............................................. 1005662

(51) Int. Cl.⁷ ................................................. A61B 5/00
(52) U.S. Cl. ........................................ 600/585; 604/529
(58) Field of Search ................................ 600/410, 411, 600/420, 423, 434, 585, 435; 604/280, 282, 264, 523, 528, 529; 606/15

(56) References Cited

U.S. PATENT DOCUMENTS

| | | |
|---|---|---|
| 4,504,268 A | 3/1985 | Herlitze |
| 4,832,023 A | 5/1989 | Murphy-Chutorian et al. |
| 4,989,608 A | 2/1991 | Ratner |
| 5,131,407 A | 7/1992 | Ischinger et al. |
| 5,154,179 A | 10/1992 | Ratner |
| 5,217,026 A | 6/1993 | Stoy et al. |
| 5,251,640 A | 10/1993 | Osborne |
| 5,290,275 A * | 3/1994 | Kittrell et al. ................. 606/15 |
| 5,439,000 A | 8/1995 | Gunderson et al. |
| 5,470,330 A * | 11/1995 | Goldenberg et al. ........... 606/7 |
| 5,514,128 A | 5/1996 | Hillsman et al. |
| 5,601,087 A | 2/1997 | Gunderson et al. |
| 5,690,120 A | 11/1997 | Jacobsen et al. |
| 5,728,079 A | 3/1998 | Weber et al. |
| 5,908,410 A | 6/1999 | Weber et al. |
| 5,951,494 A * | 9/1999 | Wang et al. ................. 600/585 |
| 5,989,243 A * | 11/1999 | Goldenberg ................... 606/7 |
| 6,099,485 A * | 8/2000 | Patterson .................... 600/585 |

FOREIGN PATENT DOCUMENTS

| | | |
|---|---|---|
| EP | 0 317 091 A3 | 5/1989 |
| EP | 0 519 604 A2 | 12/1992 |
| EP | 0 597 341 A1 | 5/1994 |
| EP | 0 744 186 B1 | 11/1996 |
| WO | WO 96/26671 | 6/1996 |

* cited by examiner

Primary Examiner—Brian L. Casler
(74) Attorney, Agent, or Firm—Michael W. Montgomery

(57) ABSTRACT

A guidewire compatible for use with magnetic resonance systems is made from a non-metallic material with a high specific electric impedance, preferably constructed primarily of a glass body. Possible material selections for the glass body include quartz. Further enhancements to the present invention are as follows. Moreover, the glass body may be sheathed in a protective polymer layer, which is also non-metallic and tends to improve the physical characteristics of the guidewire. The sheath may preferably be reinforced with a number of reinforcing fibers, which may be made from carbon, borium, aramide and also various types of glass fibers. If necessary to obtain the desired physical performance of the guidewire, including high flexibility at the distal end, a distal portion of the guidewire may be constructed of metal components according to designs known in the art. Such a metal tip portion may be made of nitinol, and should be substantially shorter than the wavelength of the magnetic resonance field.

15 Claims, 3 Drawing Sheets

GLASS CORE GUIDEWIRE COMPATIBLE WITH MAGNETIC RESONANCE

BACKGROUND AND SUMMARY OF THE INVENTION

1. Technical Background:

The present invention relates generally to intravascular medical devices, and more particularly, to a medical guidewire for use with magnetic resonance systems. Such guidewires may be used in medical procedures for both diagnostic and interventional purposes.

2. Discussion:

Guidewires are used in a wide variety of medical procedures, most often in conjunction with one or more other medical devices, including catheters. Such a catheter may be any of various types, such as angiography or angioplasty, but should in any event have a tubular lumen or other guiding means through which the guidewire can be advanced or withdrawn.

Structurally, guidewires are often long, thin metal wires that generally taper from one diameter at a proximal end which remains outside the body of the patient, to a smaller diameter at the opposite distal end. Specifically, vascular guidewires are often more than five feet long and have a maximum outer diameter of approximately 0.038 inches. The diameter of the core wire is generally ground down precisely in a series of alternating tapering portions and constant diameter sections, to develop a selectively engineered flexibility profile along the length of the guidewire.

The guidewire distal tip is usually very flexible, both to avoid vascular trauma and so that it can be selectively bent and twisted to advance it along a desired vascular path. Guidewires a redesigned to resist this twisting force or torsion, so that as the guidewire proximal end is twisted or rotated, the distal tip tends to rotate through about the same angle. In addition, a floppy spring is often affixed to the extreme distal tip of the guidewire for flexibility.

A good example of a current guidewire is described in the commonly assigned U.S. Pat. No. 4,846,186, issued to Box et al. on Jul. 11, 1989, which is incorporated in this disclosure by reference. The Box patent shows a guidewire suitable for both diagnostic and therapeutic or interventional procedures, having a Teflon coating from the proximal end along a majority of its length. The core wire tapers in steps to a distal portion that is flattened and surrounded by a flexible spring, which is brazed to the extreme distal end of the core wire to form a rounded tip.

As the body of the patient is of course opaque, physicians commonly use fluoroscopy or X-ray video cameras to track the position of the guidewire and to construct real-time images of the patient's vasculature. The visibility and brightness of selected portions of the guidewire is a relatively important feature, as described in the commonly assigned U.S. Pat. No. 5,259,393, issued to Corso, Jr. et al. on Nov. 9, 1993, and U.S. Pat. No. 5,267,574, issued to Viera et al. on Dec. 7, 1993. Both of these patents are incorporated in this disclosure by reference. In the Corso patent, the flexible spring at the guidewire distal tip is arranged to selectively control its brightness on an X-ray fluoroscope, or radiopacity. Likewise, the Viera patent discloses a plastic sleeve shrunk around an intermediate section of the guidewire, and several radiopaque marker bands.

In contrast to fluoroscopy, another method of visualizing the patient is magnetic resonance imaging, referred to as MRI. Other medical fields, such as neurology, often use procedures which are performed under MRI instead of X-ray fluoroscopy. Accordingly, it is also desirable to image the anatomy and to track the position of intravascular devices, including catheters and guidewires, using magnetic resonance (MR) systems.

For these applications, it is desirable to make guidewires usable and compatible with MRI techniques. However, a metal guidewire may be too visible under MR, brightly washing out the screen and obscuring important features. This halo phenomenon is called an "artifact," and renders the image useless. Another issue with the use of a metal guidewire under MR is the induction of eddy currents in the metal, caused by distortion of the magnetic field. These eddy currents can generate heat and may increase the local temperature of the surrounding tissue and body fluids, thus possibly damaging the tissue or causing the blood to coagulate.

It is an object of the present invention to provide a guidewire having the desired physical features, including torsion and flexibility, while also avoiding the creation of undesirable artifacts in the MR image or the generation of heat.

The present invention provides a guidewire compatible for use with magnetic resonance systems, made from a non-metallic material with a high specific electric, impedance. Accordingly, this material will resist any electrical eddy currents in the guidewire from being generated by variations in the high-frequency field. An acceptable class of materials is glass, which are all electrical insulators. A guidewire having a major portion constructed of a glass material should therefore have the advantages of not disturbing the MR field and images, as well as resisting the generation of heat.

These and various other objects, advantages and features of the invention will become apparent from the following description and claims, when considered in conjunction with the appended drawings.

DETAILED DESCRIPTION OF THE PREFERRED EMBODIMENT

The following description of the preferred embodiments of the present invention is merely illustrative in nature, and as such it does not limit in any way the present invention, its application, or uses. Numerous modifications may be made by those skilled in the art without departing from the true spirit and scope of the invention.

Figure 1:
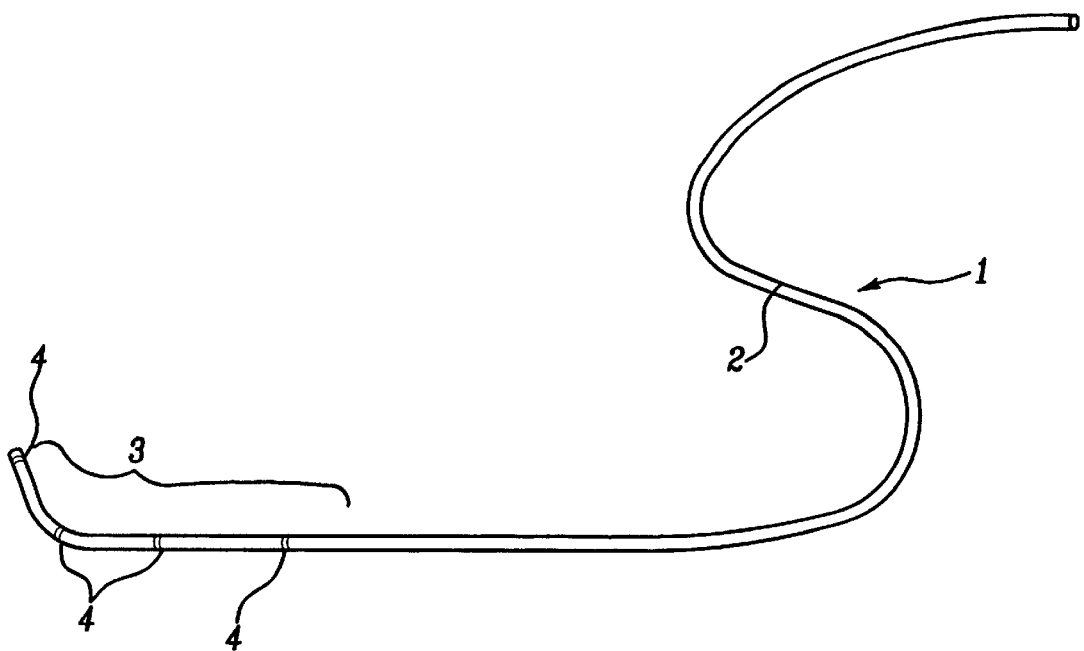
FIG. 1 is a perspective view of a guidewire for use with magnetic resonance systems, arranged according to an embodiment of the present invention.

Referring to FIG. 1, a perspective view of a guidewire according to a first preferred embodiment of the present invention is shown generally at 1. The medical guidewire 1 is intended for use in intravascular medical procedures involving the use of magnetic resonance systems, including both magnetic resonance imaging and magnetic resonance tracking of the guidewire's position within the body of the patient. Guidewire 1 is constructed of a basic body 2 and a distal tip portion 3. The distal tip of guidewire 1 includes several markers 4 embedded in the distal tip portion 3, which are more visible under MR than the remainder of the guidewire.

Figure 3:
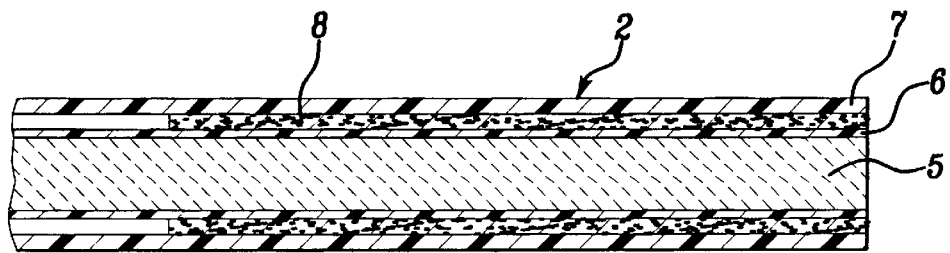
FIG. 3 is a cross-sectional view of a portion of the guidewire of FIG. 1, in a location near that indicated by arrow III.
Figure 4:
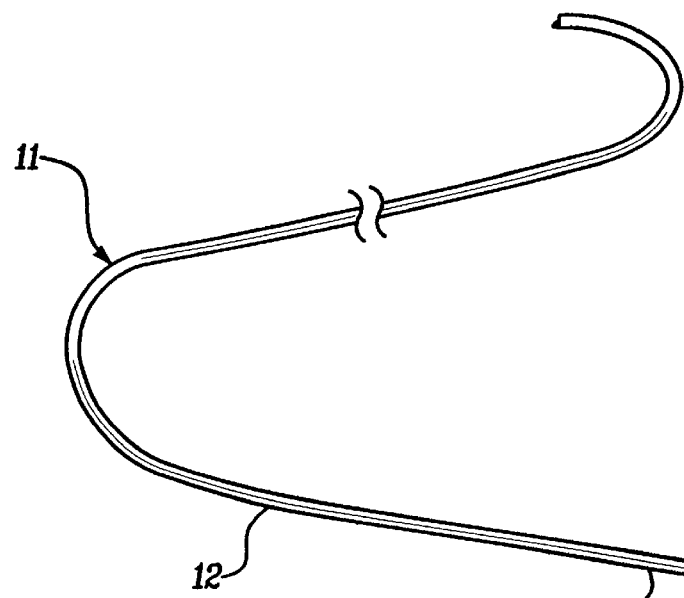
FIG. 4 is a perspective view of a guidewire for use with magnetic resonance systems, arranged according to another embodiment of the present invention.
Figure 5:
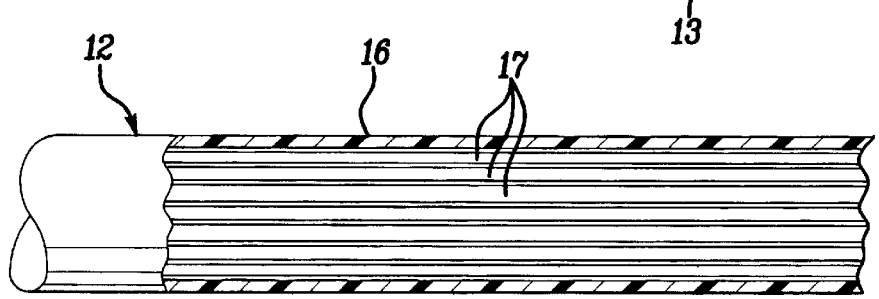
FIGS. 5–7 are cross-sectional views of a portion of various guidewires arranged according to certain embodiments of the present invention.
Figure 6:
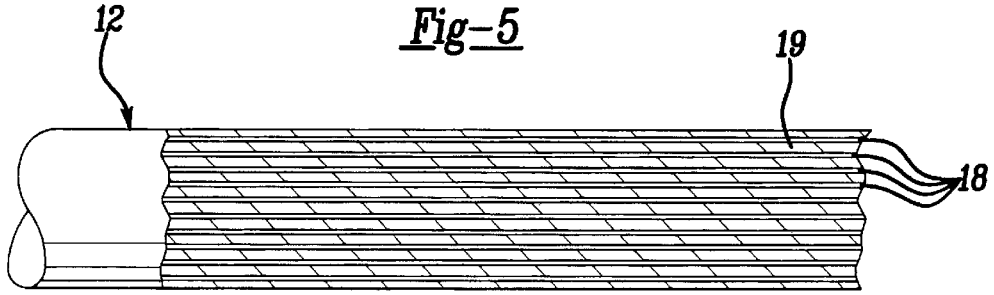
Figure 7:
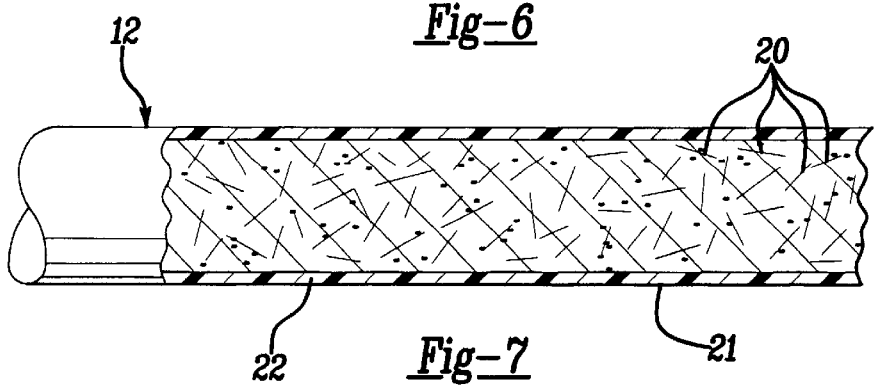
Figure 8:
FIG. 8 is a perspective view of a guidewire for use with magnetic resonance systems, arranged according to another embodiment of the present invention.
Figure 9:
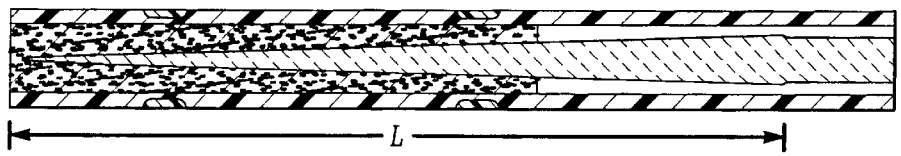
FIG. 9 is a cross-sectional view of a portion of the guidewire of FIG. 8, in a location near that indicated by arrow IX.
Figure 10:
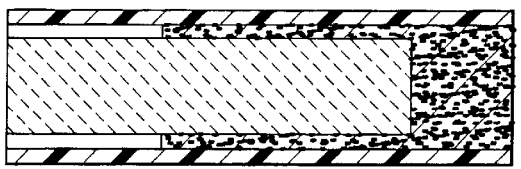
FIG. 10 is a cross-sectional view of a portion of the guidewire of FIG. 8, in a location near that indicated by arrow X.
Figure 11:
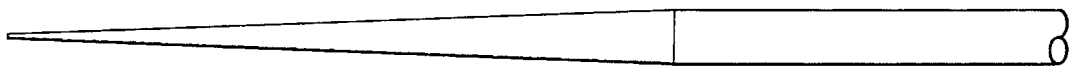
FIGS. 11–13 are side elevation views of distal portions of guidewires arranged according to alternative embodiments of the present invention.
Figure 12:
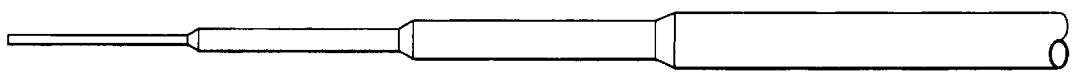
Figure 13:
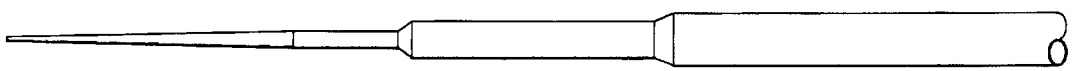

The proximal portion of the basic body 2 is illustrated in FIG. 3, and incorporates a relatively long, thin core or glass body 5, which may be encased with a protective coating or cladding 6 for improving the break strength of the glass body 5. The cladded glass body 5 extends for substantially the length of the guidewire and is surrounded with a polymer sheath 7, which is adhered to the glass body 5 with a glue 8.

Markers 4 are visible under MR because their magnetic susceptibility differs to a controlled extent from the remainder of the guidewire and surrounding body tissue, thus distorting the uniformity of the magnetic resonance field and causing the magnetic field to become what is called "locally inhomogeneous." The material of the markers 4 is selected specifically for this property, and acceptable materials include Dysprosium Oxide ($Dy_2O_3$).

The glass body 5 is preferably made of a glass material having a high specific electric impedance, such as fiberglass, silica, or quartz.

The cladding 6 adds strength to the glass core 5, in that the coating allows the glass core 5 to be bent through a sharper turn or more tortuous path without breaking. Indeed, it has been found that the cladded glass core 5 may endure strain as high as 12%. A suitable material for the coating 6 has been found to be polyimide.

The outer polymer sheath 7 may be constructed from any of a variety of materials, including nylon. An additional advantage of the design of the present invention is that the polymer sheath 7 can maintain the physical integrity of the guidewire, even if the glass core 5 should unexpectedly break. Of course, the polymer sheath 7 may be provided with a lubricious or hydrophilic coating, as generally known in the art.

Figure 2:
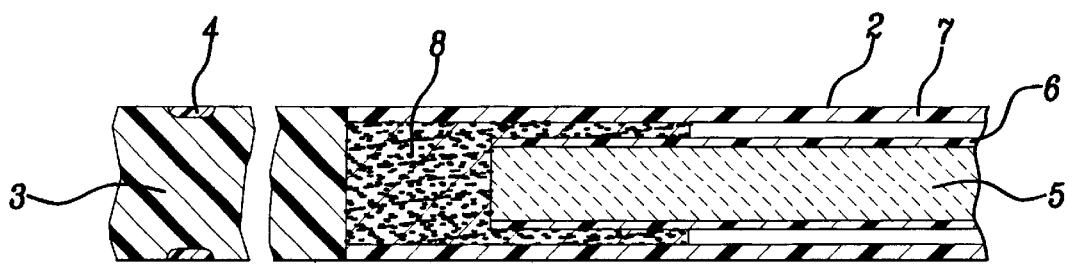
FIG. 2 is a cross-sectional view of a portion of the guidewire of FIG. 1, in a location near that indicated by arrow II.

An intermediate portion of the guidewire is depicted in FIG. 2, which focuses on a region near the transition at arrow II between the glass core proximal portion of the basic body, referred to as the "transition point."

The distal tip portion 3 of the guidewire 1 may be formed of a glass or plastic, as shown in FIG. 2, or of a metal as shown in FIGS. 8–13. The outer diameter of guidewire 1 preferably tapers to a smaller diameter toward the distal tip, as illustrated in FIGS. 8–13. The metal tip portion may be a material having a selected magnetic susceptibility, such as stainless steel, nickel titanium (nitinol), or tantalum. Preferably, the length of the metal distal tip segment is substantially shorter than the wavelength of the magnetic resonance field in which the guidewire is used.

The glue 8 is preferably of a type that cures upon exposure to ultraviolet light. Accordingly, the polymer sheath 7 should be transparent, to allow the glue 8 to be exposed to the ultraviolet light after portions of the guidewire I are assembled as shown in FIGS. 1–3.

An alternative embodiment of the present invention is depicted in FIGS. 4–7, in which a guidewire 11 has a proximal portion 12 and a distal tip portion 13. Guidewire 11 has a plastic sheath 16 in which a number of reinforcing fibers have been embedded. Sheath 16 may be shrunk around a bundle of fibers 17, or the sheath 16 may be braided with the reinforcing fibers. Alternatively, fibers 18 may be embedded in a polymer matrix 19 In addition, a multiplicity of short reinforcing fibers 20 can be provided in a polymer matrix 21, surrounded by a coating 12. The reinforcing fibers may be of any suitable material, such as carbon, borium, aramide, or glass.

The guidewire of the present invention may also be constructed of more than one glass core body, all of which may be clad as a unit with a single protective coating.

It should be understood that an unlimited number of configurations for the present invention can be realized. The foregoing discussion describes merely exemplary embodiments illustrating the principles of the present invention, the scope of which is recited in the following claims. Those skilled in the art will readily recognize from the description, claims, and drawings that numerous changes and modifications can be made without departing from the spirit and scope of the invention.

What is claimed is:

1. A medical guidewire having a length greater than 24 inches for use in intravascular medical procedures and compatible with magnetic resonance, the guidewire having proximal and distal ends, comprising:

at least one thin core fiber extending for substantially the length of the guidewire, the core fiber being made of a glass having a high specific electric impedance; wherein a distal segment of the glass core fiber tapers to a diameter at its distal end that is smaller than the diameter of a major portion of the core fiber;

a polymer sheath surrounding the core fiber, and which is affixed to the core fiber at least at a proximal and a distal end with an adhesive; wherein the core fiber has a breaking strength, said core fiber being covered with a cladding for increasing said breaking strength and;

at least one marker positioned near a distal end of the guidewire, wherein the marker is visible under magnetic resonance due to susceptibility-induced magnetic field inhomogeneity, and wherein the guidewire is formed substantially entirely of non-metallic materials.

2. The medical guidewire of claim 1, further comprising a plurality of reinforcing fibers affixed to the core to enhance the flexibility and torsion characteristics of the guidewire.

3. The medical guidewire of claim 1, further comprising a plurality of reinforcing fibers affixed to the polymer sheath to enhance the flexibility and torsion characteristics of the guidewire.

4. The medical guidewire of claim 3, wherein the material of the reinforcing fibers is selected from the group consisting of carbon, borium, aramide, and glass.

5. The medical guidewire of claim 1, wherein the material of the core is selected from the group consisting of fiberglass, silica, and quartz.

6. The medical guidewire of claim 1, wherein the material of the marker Dysprosium Oxide ($Dy_2O_3$).

7. The medical guidewire of claim 1, wherein the distal tip of the guidewire is bent slightly, to facilitate the selective steering of the guidewire along a desired vascular path.

8. The medical guidewire of claim 1, wherein at least a portion of the polymer sheath has a hydrophilic coating.

9. The medical guidewire of claim 1, wherein the core is formed of a plurality of glass core strands.

10. A medical guidewire having a length greater than 24 inches for use in intravascular medical procedures and compatible with magnetic resonance, the guidewire having proximal and distal ends, comprising:
   a thin core extending for substantially the length of the guidewire, the core being made of a glass having a high specific electric impedance;
   a polymer sheath surrounding the core;
   at least one marker positioned near a distal end of the guidwire, wherein the marker is visible under magnetic resonance due to susceptibility-induced magnetic field inhomogeneity; and
   a distal tip segment made substantially entirely of metal components affixed to the glass core at a transition point, wherein a length of the relatively short distal tip segment is shorter than a wavelength of a magnetic resonance field in which the guidewire is used; wherein a remainder of the guidewire other than the distal tip segment is formed substantially entirely of non-metallic materials.

11. The medical guidewire of claim 10, wherein the material of the metal distal tip segment is nitinol.

12. The medical guidewire of claim 10, wherein a distal segment of the glass core tapers to a diameter that is smaller than the diameter of a major portion of the core.

13. The medical guidewire of claim 10, wherein the polymer sheath extends continuously from a location near the proximal end of the guidewire, to a location distal of the transition point, thus surrounding at least a portion of both the glass core and the metal distal tip segment.

14. The medical guidewire of claim 10 further comprising a short metal collar affixed to the guidewire at the transition point, to resist kinking and breakage of the guidewire at the transition point.

15. The medical guidewire of claim 10 wherein the core has a breaking strength, said core being covered with a cladding for increasing said breaking strength.

* * * * *